(12) United States Patent
Sutherland et al.

(10) Patent No.: US 8,424,517 B2
(45) Date of Patent: Apr. 23, 2013

(54) MEDICAMENT DELIVERY DEVICES

(75) Inventors: Garth Campbell Sutherland, Auckland (NZ); Michael James Gormack, Auckland (NZ)

(73) Assignee: Nexus6 Limited, Auckland (NZ)

( * ) Notice: Subject to any disclaimer, the term of this patent is extended or adjusted under 35 U.S.C. 154(b) by 628 days.

(21) Appl. No.: 12/567,182

(22) Filed: Sep. 25, 2009

(65) Prior Publication Data

US 2010/0252036 A1   Oct. 7, 2010

(30) Foreign Application Priority Data

Apr. 1, 2009   (NZ) ........................................ 575943

(51) Int. Cl.
*A61M 11/00* (2006.01)

(52) U.S. Cl.
USPC ............ 128/203.12; 128/200.14; 128/200.23; 128/205.23

(58) Field of Classification Search ............. 128/200.14, 128/200.23, 202.22, 205.23, 203.12
See application file for complete search history.

(56) References Cited

U.S. PATENT DOCUMENTS

| | | | |
|---|---|---|---|
| 4,984,158 A * | 1/1991 | Hillsman ................ | 128/200.14 |
| 5,363,842 A | 11/1994 | Mishelevich et al. | |
| 5,544,647 A | 8/1996 | Jewett et al. | |
| 5,809,997 A * | 9/1998 | Wolf ........................ | 128/200.23 |
| 6,202,642 B1 * | 3/2001 | McKinnon et al. ...... | 128/200.23 |
| 6,294,999 B1 | 9/2001 | Yarin et al. | |
| 6,958,691 B1 * | 10/2005 | Anderson et al. ........ | 340/539.12 |
| 7,065,409 B2 * | 6/2006 | Mazar ............................ | 607/60 |
| 7,151,456 B2 | 12/2006 | Godfrey | |
| 2005/0028815 A1 | 2/2005 | Deaton et al. | |
| 2005/0119604 A1 | 6/2005 | Bonney et al. | |
| 2007/0163583 A1 | 7/2007 | Brand et al. | |

FOREIGN PATENT DOCUMENTS

| | | |
|---|---|---|
| WO | 95/22365 | 8/1995 |
| WO | 2008/112353 | 9/2008 |

* cited by examiner

*Primary Examiner* — Steven Douglas
(74) *Attorney, Agent, or Firm* — Davidson, Davidson & Kappel, LLC

(57) ABSTRACT

The invention relates to improvements in or relating to medicament delivery devices. In particular, this invention relates to a communications device which may be fitted to an electronic medicament delivery device. The invention may be particularly suitable for use with electronic medicament inhalers such as those used for the treatment of diabetes, or respiratory diseases such as asthma, COPD, cystic fibrosis, and bronchiectasis.

19 Claims, 5 Drawing Sheets

MEDICAMENT DELIVERY DEVICES

This application claims priority to New Zealand Patent Application No. 575943, filed Apr. 1, 2009, the contents of which are hereby incorporated by reference in their entirety.

TECHNICAL FIELD

This invention relates to improvements in or relating to medicament delivery devices. In particular, this invention relates to a communications device which may be fitted to an electronic medicament delivery device. The invention may be particularly suitable for use with electronic medicament inhalers such as those used for the treatment of diabetes, or respiratory diseases such as asthma, COPD, cystic fibrosis, and bronchiectasis. However, it is to be understood and appreciated that the invention is not to be limited to such use. The prior art and possible applications of the invention, as discussed below, are therefore given by way of example only.

BACKGROUND OF THE INVENTION

Electronic medicament inhalers are widely used for the treatment of respiratory diseases such as asthma, COPD, cystic fibrosis, and bronchiectasis. They are also becoming more prevalent for dispensing insulin for people with diabetes.

A common type of medicament inhaler is what is known as a pressurised Metered Dose Inhaler (pMDI). Such inhalers generally comprise a medicament canister and an actuator. The medicament canister contains medicament under pressure and is designed to deliver a metered dose of medicament in the form of an aerosol spray. The actuator generally comprises a substantially L-shaped hollow tube which has a first open end adapted to receive the medicament canister, and a second open end which acts as a mouth piece.

Medicament canisters for use with a pMDI generally have a spray stem extending from one end which is adapted to engage with a spray-directing element housed within the actuator, and adjacent to the mouth piece of the actuator. When the canister is pushed down into the actuator, the spray stem and spray-directing element combine to direct a metered dose of medicament out through the mouthpiece and into the mouth of the user.

Another common type of medicament inhaler is what is known as a Dry Powder Inhaler (DPI). DPI's are generally in the form of a disc or grinder which may be rotated in order to dispense a metered dose of dry powder into an appropriate receptacle or mouthpiece, from where it may then be inhaled by the user (for example, by sucking strongly on the mouthpiece of the inhaler).

Some medicament inhalers are kept on hand for use in a specific event or emergency. For example, if a person were to have a sudden asthma attack, they may reach for a medicament inhaler which contains what is generally known as a "reliever" medicament. A reliever medicament is fast acting and in most cases will relieve (or reduce the severity of) the asthma attack, almost instantaneously.

Other medicament inhalers are designed for regular use in order to prevent an event such as an asthma attack and/or to manage or control a disease such as asthma. Such inhalers are generally known as "preventers" because the regular use of such inhalers serves to prevent (or minimise the likelihood of) an asthma attack. The regular use of preventer medicament by asthma sufferers is generally effective in controlling the disease and/or preventing the vast majority of asthma attacks.

Commonly, preventer medicament for asthma sufferers is taken twice a day, usually at a set time in the morning and in the evening.

There are now also available "combination" medicament inhalers which combine both a reliever and preventer medicament, with a view to controlling the respiratory disease (with the preventer medicament), when a patient uses their reliever medicament for symptom alleviation.

Studies have shown that many people demonstrate poor disease management, for example by overusing their reliever medicament. The overuse of a reliever medicament has the potential to reduce the effectiveness of the medicament, which may render the medicament less effective in times of real need, for example during a severe asthma attack.

Moreover, a patient's increased use of reliever medicament over a period of time may be indicative of a pending exacerbation event.

A problem or difficulty associated with the use of preventer (or "combination") medicament inhalers is poor medicament compliance. That is, many studies have shown that users frequently do not take their medicament at the predetermined or prescribed times and/or in the required amounts. This is a particular problem amongst young children, the elderly, or people of reduced mental capacity.

The consequences of this non-compliance are reduced disease control, lower quality of life, lost productivity, hospitalisation and avoidable deaths.

Furthermore, during clinical trials (for example, to test a new preventer medicament), it is important (for the trial to be accurate and/or successful) that the patients in the trial take their medicament at the prescribed times and/or in the prescribed amounts.

Not only is compliance to preventative medicaments typically low, but it has also been shown that actual compliance by a user is lower than the same user's estimated compliance.

To order to address these problems and difficulties, there are presently available a number of electronic medicament inhalers which include compliance monitoring means.

Most compliance monitoring means include, at the very least, dose counting means. For example, see U.S. Pat. No. 5,544,647 (Jewettt et al), U.S. Pat. No. 6,202,642 (McKinnon et al) and US Patent Publication No. 2005/0028815 (Deaton et al).

Furthermore, some presently available electronic medicament inhalers also include means to record a range of compliance data, in addition to dose counting. For example, McKinnon includes an electronics module to record date and time as well as more comprehensive patient usage information.

U.S. Pat. No. 5,363,842 (Mishelevich et al) describes a device which also monitors patient inhalation data, for example how much air is inhaled through the inhaler and with what time course. The resultant data may be transmitted to a remote location such as a health care professional where the inhalation data can be compared to a standard target envelope, and the success or otherwise of the patient's inhalation may then be signaled back to the patient. Mishelevich also monitors for other patient usage data such as whether the medicament inhaler was shaken prior to use.

The patient usage (or compliance) data gathered by such electronic medicament inhalers may be managed or used in various ways.

For example, Deaton displays the patient usage data on a display which is integrally formed with the device. This has limitations in that the patient usage data is only able to be viewed by the user, whereas it would be of more benefit to have the data viewed and/or monitored by a third party such as a care giver or a medical professional.

Jewett includes both an LCD display for displaying patient usage data on the device, as well as a memory for storing data which may later be downloaded to a printer via a terminal. McKinnon describes a docking station which is adapted to receive the electronic medicament inhaler, and retrieve the patient usage data from the inhaler.

A disadvantage associated with Jewett, Deaton and McKinnon is that the patient usage data is not able to be transmitted wirelessly (preferably to a remote location) and/or in real time. Instead, the patient usage data is only able to be downloaded periodically, and at the sole discretion of the user. There is also no provision for the two-way transmission of data.

An advantage of monitoring patient usage data in real time (or at frequent time intervals) is that the patient usage data is always current, and hence anyone viewing or wishing to have access to the data will feel more comfort knowing this. Furthermore, any potential overuse or underuse of the medicament delivery device may be immediately apparent, and (for example) any appropriate alerts may be made to the patient (or to a third party such as a care giver or medical professional). Real time (or frequent) monitoring may also be able to predict a potential exacerbation event, prior to the event occurring.

An advantage associated with the wireless transmission of data, is that the data may be transferred to a remote monitoring location, for example via a mobile phone network to the internet and/or a network computer system. The remote monitoring location may be, for example, a medical professional whereby the medical professional may continuously monitor patient usage or compliance data.

PCT Patent Application No. PCT/US2008/052869 (Levy et al) describes a sleeve housing (24) which is attachable to an actuator body (12). The sleeve housing includes electronic monitoring apparatus and the device is designed to monitor patient usage data, with a view to being able to predict an exacerbation event before it occurs. To facilitate this, Levy discloses the use of wireless technology to transmit the patient usage data. However, Levy relies on a counting means which requires attachment of a cap 28 to the canister (16) which is adapted to engage with a dose-dispensing sensor (26) during the delivery of a dose of medicament. Hence, Levy requires modifications to the inhaler prior to being able to be used. The fitting of the Levy device to an inhaler may therefore be a fiddly and time consuming operation. Furthermore, any modifications made to an inhaler have the potential to interfere with the medicament delivery ability or effectiveness of the inhaler. The Levy device is also not adapted to be fitted to an inhaler which already has electronic compliance monitoring means.

U.S. Pat. No. 6,958,691 (Anderson et al) describes a device for the delivery of medicament which includes a medicament inhaler with an electronic data management system. The Anderson device includes an integral communicator which provides for two-way wireless communication between the electronic data management system and a network computer system. The communication may be in real time.

However, a disadvantage associated with Anderson is that the wireless communication system is integrally formed within the actuator housing. The cost of incorporating such a wireless communication system into each and every inhaler is significant and hence the cost of such a device may be prohibitive.

Furthermore, because the compliance monitoring device is integrated within the medicament inhaler, it cannot generally be reused for longer than the life of the inhaler. Given that each inhaler typically contains a one month supply of medicament, it is economically and environmentally wasteful to supply and then discard such technology with each month's medication.

Recent advances in modern manufacturing techniques are now making it feasible and cost effective, to mass-produce disposable electronic inhalers. That is, each disposable electronic inhaler may include its own (relatively basic) electronic compliance monitoring means (the minimum monitoring means likely being a dose counter and real time clock to record the date/time of each dose of medicament delivered). Whilst this is of advantage given that more people will be able to afford, or have access to, such compliance monitoring means, the problem remains on how to display and/or transmit the patient usage data gathered.

Having regard to the foregoing, it would therefore be of advantage if there was available a communications device which was able to be fitted to an electronic medicament delivery device, such as an electronic inhaler, and whereby the communications device had the ability to wirelessly transmit data gathered by the electronic medicament delivery device to a desired location.

OBJECT

It is an object of the present invention to provide a communications device for use with an electronic medicament delivery device which goes some way towards addressing the aforementioned problems or difficulties, or which at the very least provides the public with a useful choice.

DEFINITIONS

Throughout this specification unless the text requires otherwise, the word 'comprise' and variations such as 'comprising' or 'comprises' will be understood to imply the inclusion of a stated integer or step or group of integers or steps but not the exclusion of any other integer or step or group of integers or steps.

Throughout this specification, the term "patient" when used in relation to a medicament delivery device, is to be understood to refer to any person that uses a medicament delivery device.

SUMMARY OF THE INVENTION

According to one aspect of the present invention, there is provided a reusable and portable communications device for receiving and transmitting data relating to patient usage of an electronic medicament delivery device, said electronic medicament delivery device including:
  a) a supply of medicament,
  b) a medicament dispensing means,
  c) data gathering means for gathering data relating to patient usage of said electronic medicament delivery device,
  and wherein said communications device includes:
  d) a housing, said housing able to be releasably fitted to said electronic medicament delivery device;
  e) data collection means associated with said housing to receive said data from said electronic medicament delivery device,
  f) a wireless communicator associated with said housing to enable the wireless transmission of said data.

DETAILED DESCRIPTION

Figure 1:
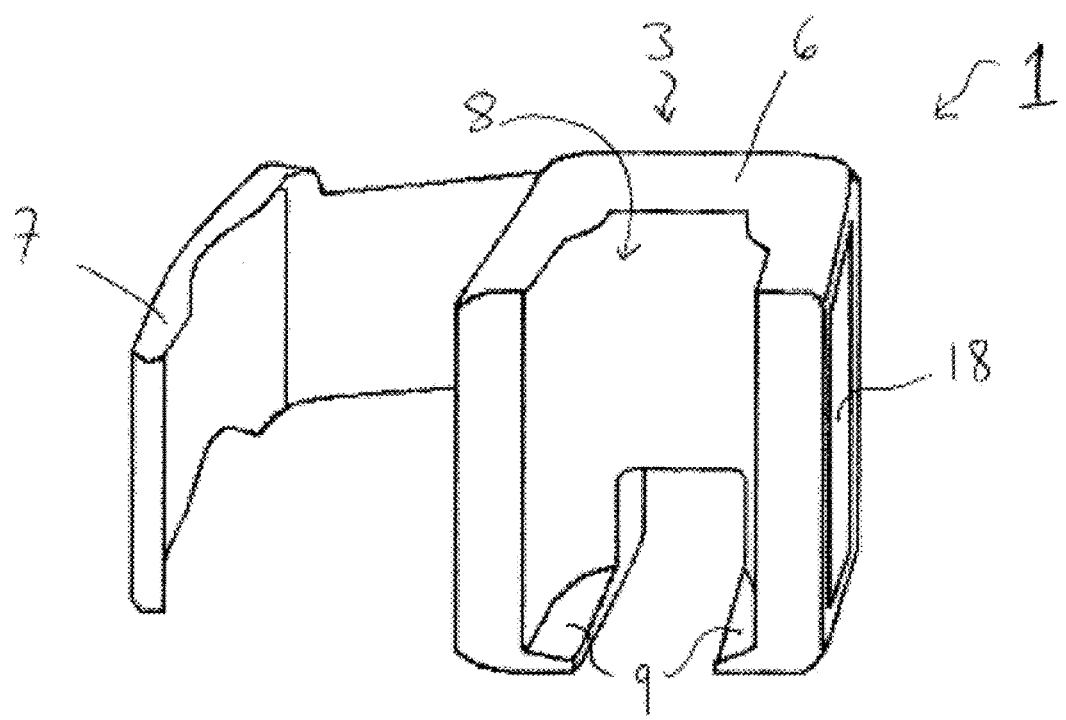
FIG. 1: is a front perspective view of one possible embodiment of a communications device for use with the present invention.

The "data" relating to patient usage of the medicament delivery device may include (but is not limited to) any or all data or information relating to the patient; the environment (eg, temperature or humidity); the medicament; the delivery of the medicament; the quantity of medicament delivered; patient compliance data; the medicament delivery device; any physiological criteria of a patient (eg, peak flow data, inhalation data or blood glucose level data); any programs or algorithms associated with the system; any data or instructions sent or received by any component of the system; the results of any operations on any of the aforesaid data.

Any type of electronic medicament delivery device is within the scope of this invention. An electronic medicament delivery device may be any medicament delivery device which includes an electronic component, for example an electronic dose counter and/or a real time clock and/or a memory and/or a user interface and/or a LCD screen and/or audio-visual reminder means, and/or a battery and so on.

Examples of electronic medicament delivery devices for use with the present invention include (but are not limited to): devices for delivering a dose of insulin; nasal sprays; nebulisers; transdermal devices; inhalation devices; pill boxes or containers (eg see U.S. Pat. No. 6,294,999 (Yarin et al)).

For convenience only, the electronic medicament delivery device may be predominantly referred to herein as "medicament delivery device".

Any type of medicament may be utilised, as required or as desired or as dictated by the nature of the medicament delivery devices and/or the disease being treated. The medicament may be dispensed in any suitable or desired form, eg as a liquid, a solid, a powder, a spray, a gas, or an aerosol, and so on.

Any suitable medicament dispensing means may be utilised which enables the patient to receive a dose(s) of medicament.

The medicament delivery device may preferably be adapted to deliver a metered dose of medicament, although the delivery of a non-metered dose of medicament is also within the scope of the invention.

Preferably, the medicament delivery device may be a medicament inhaler, such as a pMDI or a DPI, and preferably an integrated electronic medicament inhaler. Examples of such electronic medicament inhalers include those used for administering a dose(s) of insulin for treatment of diabetes, or inhalers used for the treatment of respiratory diseases such as asthma, COPD, cystic fibrosis, and bronchiectasis.

Electronic medicament delivery devices are well known in the prior art (for example, Jewett, McKinnon, Deaton, Levy, Mishelovich and Anderson are all electronic medicament delivery devices). It is not intended therefore (or considered necessary) to include an overly detailed description of such devices per se, as their workings and operation will be well known to those skilled in the art.

The data gathering means may be any suitable means for gathering data in relation to the patient usage of the electronic medicament delivery device Preferably, the data gathering means includes, at the very least, dose counting means in the form of a dose counter and a real time clock (which may record the date/time of each delivery of a dose of medicament).

The data gathering means may also include means for monitoring for any additional patient usage (or compliance) data. Examples include (but are not limited to) data such as inhalation data; peak flow data; blood/glucose levels; quantity of medicament dispensed; environmental conditions such as temperature and humidity; whether the medicament delivery device was shaken prior to use; as well as data relating to the patient, the medicament or the medicament delivery device itself.

The electronic medicament delivery device may also include some or all of the common features associated with such presently available devices, Examples include (but are not limited to) a user interface, a LCD screen, a battery, and/or audio/visual notification means to notify or remind the patient of a particular event.

The medicament delivery device may preferably include a first data storage means for the storage of patient usage data. The data storage means may preferably include memory in the form of RAM or ROM.

The medicament delivery device may include an electronic control module for controlling the operation of the medicament delivery device and/or for performing operation(s) on the data. Such electronic control modules are known in the prior art (eg McKinnon and Anderson).

For example, the electronic control module may serve to manage the settings or operational configurations of the medicament delivery device such as date/time and/or the timing of any alarms or notifications. The electronic control module may also have the ability to increase or decrease the amount of medicament dispensed by the medicament delivery device, for example the quantity of medicament dispensed per dose. The electronic control module may do this by sending a signal to the dose dispensing means to alter the quantity of medicament dispensed per dose. The electronic control module may also have the ability to prevent the medicament dispensing means from dispensing a dose(s) of medicament for a predetermined time period (this may be particularly important for dispensing pain medication—where the nature of the medicament often makes the patient susceptible to taking too much medicament or possibly even becoming addicted to the medicament).

Preferably, any such instructions for the electronic control module associated with the medicament delivery device may come from a third party (or the patient) via the communications device (once fitted to the medicament delivery device). Alternatively and/or additionally, the patient may use the user interface associated with the medicament delivery device to change the settings of the medicament delivery device via the electronic control module.

The electronic control module may also include a micro processor for performing operations on the data gathered.

Such micro processors for use with medicament delivery devices are known in the prior art (eg Mishelevich and Anderson).

As part of its make up, the electronic control module may include a microcontroller and/or an Application Specific Integrated Circuit (ASIC) and/or a set of digital logic gates.

In one embodiment, the data gathering means may be a stand alone component, which gathers data relating to patient usage of the medicament delivery device, and which is adapted or able to forward the data thus gathered to the data storage means.

Alternatively, the data gathering means may comprise part of the electronic control module.

The real time clock may be incorporated within the data gathering means or alternatively it may comprise part of the electronic control module.

The first data storage means may also be able to store data resulting from any operations performed on the patient usage data, for example by the microprocessor. The data storage means may also be able to store data relating to any instructions or data received from the communications device, for example any instructions received for the electronic control module to limit or increase the amount of medicament to be dispensed or to set an alarm.

The communications device may preferably include a housing which is able to be fitted to the medicament delivery device.

The housing may preferably include a second data storage means for storing the data received from the medicament delivery device. The second data storage means may also serve to store any data or instructions received by the communications device, for example any data or instructions received for transmission to the medicament delivery device.

The housing may be of any suitable size, shape or configuration as required or desired, or as dictated by the type or configuration of the medicament delivery device.

In one embodiment, the housing may be portable and/or releasably attachable to the medicament delivery device. In such an embodiment it may be appreciated that the communications device may be reusable in that it may be utilised across a range of different medicament delivery devices.

For example, a patient may fit the housing to a first medicament delivery device that they have been using, in order to receive the data from the medicament delivery device and transmit it to a desired location. The patient may then remove the housing from the medicament delivery device and fit it to a second medicament delivery device that the patient has also been using, to also receive the data from the second medicament delivery device and also transmit it to a desired location. Alternatively, or additionally, a medical practitioner may provide a patient with a communications device to use for a predetermined time period (for example, so the medical practitioner can assess patient usage data to determine any shortcomings in the patient's treatment regimen). After the predetermined time period has expired the patient may return the communications device whereby the medical practitioner may then make it available to another patient.

Alternatively or additionally, once a medicament delivery device has exhausted its supply of medicament, the communications device may be removed from the medicament delivery device and releasably fitted to either another medicament delivery device or to the same medicament delivery device with a replacement supply of medicament added.

The housing may preferably be adapted to be fitted to the medicament delivery device, and subsequently be operable, without any modifications being required to the medicament delivery device. This allows for ease of use of the communications device.

In one embodiment, the housing may be in the form of a sleeve adapted to be fitted around the outside of the medicament delivery device.

The housing may be adapted to partially enclose and/or partially contain the medicament delivery device, for example by clipping onto the medicament delivery device. For example, the housing may be in the form of a substantially U-shaped sleeve adapted to clip snugly onto or around the outside of the medicament delivery device. In such an embodiment the housing may be provided with additional means to help secure the housing to the medicament delivery device, for example by the use of ties or straps.

In another such embodiment, the housing may be adapted to fully encircle and/or fully contain the medicament delivery device. In such an embodiment, the housing may be provided with a hinged portion, which, when open, allows the medicament delivery device to be placed within the housing, and which, when closed, serves to retain and/or secure the medicament delivery device substantially within the housing. The hinged portion may be provided with closure and release means, to secure the hinged portion, and release the hinged portion, respectively. For example, the closure and release means may be provided by a suitable fastener such as a VELCRO brand fastener, or alternatively by a latch-type or snap-on or clip-on type mechanism. The closure and release means may also be provided by the hinged portion clipping onto or into an appropriately shaped portion of the housing proper.

In such an embodiment, because the communications device is designed to be portable and reusable, the communications device therefore has an indefinite lifetime (which overcomes the problem of the prohibitive cost of installing a communications device into each and every medicament delivery device, eg Anderson).

In an alternative embodiment, the communications device may be adapted to be fitted within the medicament delivery device. For example, a medicament delivery device may be provided with an appropriate aperture or compartment into which the communications device may be fitted. In such an embodiment, the communications device may be in the form of a cartridge. The aperture or compartment may be provided with a lid or cover (similar to the battery covers associated with remote controls etc). Preferably the communications device may be able to be fitted within the medicament delivery device without the need for any tools or modifications being required to either the medicament delivery device or the communications device. Alternatively, the fitting of the communications device to the medicament delivery device may require the use of tools, for example, a cover plate associated with the medicament delivery device may have to be unscrewed, prior to the communications device being fitted.

Preferably, the communications device may not interfere with, or otherwise affect, the ability of the medicament delivery device to dispense medicament, when the communications device is fitted thereto.

The housing may be made of any suitable material although a plastics material may be preferred as it is relatively light, and may be conveniently and inexpensively mass produced, for example by injection moulding technology.

The housing may be substantially opaque, translucent or transparent. For example, for aesthetic reasons the housing may be substantially opaque and of the same colour as a particular manufacturer's range of medicament delivery devices to which it is intended to be fitted.

Alternatively, the housing may be substantially transparent (or translucent) so that parts of the medicament delivery device may be inspected or viewed through the housing.

The communications device may include a user interface, for example a LCD screen and a number of operational buttons. The user interface may be used, for example, to access any data received (or transmitted) by the communications device and/or to change the settings of the communications device (for example to change the frequency of when data is uploaded from the medicament delivery device to the communications device).

Any suitable data collection means may be utilised to order to effect the transmission of data from the medicament delivery device to the communications device. The data collection means may preferably allow for the two-way transmission of data between the medicament delivery device and the communications device (so that the communications device may also be able to transmit data or instructions to the medicament delivery device, for example, instructions to increase or decrease the quantity of medicament dispensed per dose). Alternatively, the data collection means may only allow for only one-way transmission of data from the medicament delivery device to the communications device.

The data collection means may be adapted or able to facilitate the transfer of data in real time or at predetermined time intervals, for example, twice a day (in the morning and evening), or once a week, or after a certain number of doses of medicament have been dispensed.

In a first embodiment, the data collection means may include a first PCB socket associated with the communications device, with the first PCB socket being releasably engageable with a second PCB socket associated with the medicament delivery device. The arrangement and construction may be such that the mating of the first and second PCB sockets facilitates the transfer of the data from the medicament delivery device to communications device. The data may be transferred as soon as the first and second PCB sockets engage, or alternatively the data transfer may be initiated manually, for example by the patient using the user interface to facilitate the transfer.

In a second embodiment, the data collection means may include a first wireless transceiver associated with the communications device, with the first wireless transceiver being communicable with a second wireless transceiver associated with the medicament delivery device. The arrangement and construction may be such that the second wireless transceiver is able to transmit data from the medicament delivery device to the first wireless transceiver associated with the communications device. The data may be transferred as soon as the communications device is fitted to the medicament delivery device, or alternatively the data transfer may be initiated manually, for example by the patient using the user interface to facilitate the transfer.

Preferably, the first wireless transceiver may be able to receive the data from a position outside of the medicament delivery device. Hence, the communications device may be non-obtrusive in that it does not, in any way, impact upon the ability of the medicament delivery device to dispense medicament (either when the communications device is fitted thereto or subsequently removed).

The first and second wireless transceivers may utilise optical light frequencies to transmit and/or receive the data. Alternatively, the first and second transceivers may utilise infrared or RF frequencies.

The communications device may preferably include a wireless communicator to enable the wireless transmission of data.

The first transceiver may be adapted to be able to transmit the data received from the medicament delivery device to the wireless communicator, and any transmission means may be utilised to facilitate this, for example by using optical transmission means, or infrared or radio frequencies.

The data may be transmitted by the wireless communicator to any desired remote location. A remote location may be any location other than the medicament delivery device or communications device. For example a remote location may be in the vicinity of the patient or the remote location may be geographically distant.

The remote location may, for example, be a public access computer network such as the internet. In such an embodiment, the data may be sent to a specific website, for example a website belonging to a health professional, insurer or care giver.

Alternatively, the data may be transmitted to a private access computer network system such as an intranet, for example an intranet computer network system belonging to a health professional, insurer or care giver.

Alternatively, the data may be transmitted to at least one web service.

The wireless communicator may preferably be in the form of a cell phone chip embedded within the communications device. Other types of wireless transmission are also within the scope of this invention, for example RF transmissions, optical light transmissions, infrared, or transmission means such as Bluetooth®.

The communications device may further include an electronic control module for controlling the operation of the communications device and/or for controlling the operation of the medicament delivery device. For example, the electronic control module may include means for controlling operation of the medicament delivery device based on instructions received from a third party, for example instructions to increase or decrease the quantity of medicament dispensed per dose. Having such an electronic control module associated with the communications device may obviate the need for a corresponding electronic control module being associated with the medicament delivery device (substantially as described previously). This may have cost advantages in that each and every medicament delivery device may require an inbuilt electronic control module, and instead the communications device may house this feature. This may be of particular advantage in embodiments where the communications device is portable and/or releasably attachable across a range of different medicament delivery devices.

It is also envisaged that the communications device may be utilised to provide a whole range of data or instructions or information to the medicament delivery device. For example, any information or data relating to settings of the medicament delivery device and/or data relating to a patient's prescribed treatment regimen and/or data relating to the operation of the medicament delivery device.

This information or data may be provided by any party, for example the patient, a care giver, a health professional or clinical trial investigator or insurer, and so on. Some of the information may relate to a patient's desire to change the settings of the device and this may be done more easily from a PC (with which people are generally very familiar with) rather than using the user interface associated with the medicament delivery device or communications device (which the patient may find unfamiliar and/or tricky to use given its small size and generally limited function).

Examples of such data or information transmitted to the communications device and/or to the medicament delivery device, via the communications device, may include (but is not limited to):

1. Audio and/or visual reminder signals for the medicament delivery device. For example, the patient (or care giver etc) may wish to change these settings based on usage data which may result in a changed treatment regimen.
2. Information relating to dose dispensing configuration settings. For example, the quantity of medicament to be dispensed and the frequency.
3. Information about the medicament. For example, this may be sent by a health professional to the patient.
4. Information which comprises educational material for the benefit of the patient. For example, this information may include an explanation of the side effects of any medicament for patients which have shown concern in relation to using any particular type of medicament. Such information may be targeted to specific patients for particular reasons as stated. This type of information may also include regular updates, and may obviate the need for regular mail outs of information to patients which has cost saving advantages (as well as timing advantages in that the information may be received immediately by the patient after being sent electronically).
5. Instructions to stop delivery of the medicament for a specified time period. For example, if the patient usage data indicates that the patient is overusing a medicament (or if the patient has not paid for the medicament), then instructions may be sent to the medicament delivery device, via the communications device, to stop dispensing the medicament for a predetermined time period.
6. Instructions to alter the quantity of medicament delivered by the medicament dispensing means. For example, these instructions may be received by the communications device, and passed onto the electronic control module associated with the medicament delivery device, which is then able to alter the quantity of medicament dispensed.
7. Information relating to date and time information. For example, the date and time associated with the real time clock may be automatically updated from time to time—similar to how a computer's times are constantly updated automatically.
8. Information relating to data transmission configuration settings. For example, changes to when data is transmitted from the medicament delivery device to the communications device and/or from the communications device to the desired location.
9. Information including software for execution on the communications device and/or the medicament delivery device. For example, anti-virus software updates could be sent, or software to fix a bug diagnosed within the medicament delivery device, or general software improvements or updates (similar to how Microsoft regularly sends out updates to people using its software applications).
10. Information which includes user interface graphics and/or strings. For example, a new user interface structure could be sent to the communications device and/or to the medicament delivery device (for example, with larger fonts making the LCD screen easier to read for people that request it).
11. Information which includes different language settings. For example, data enabling the user interface to read in Japanese or Spanish rather than English.
12. Information which includes images. For example, the patient may wish to customise their medicament delivery device by uploading a personal photo to the LCD screen.
13. Information which includes audio files. For example, the patient may wish to customise their medicament delivery device by uploading a personal song or tune to use as a reminder ringtone.
14. Information which includes moving picture files. For example, the patient may wish to customise their medicament delivery device by uploading a personal movie to the LCD screen. Alternatively a health care professional may wish to forward an educational video.

An advantage associated with the present invention is that the significant cost of installing a wireless transmitter, such as a cell phone chip, into each and every medicament delivery device is avoided (cf: Anderson).

The communications device may also include means for transmitting its position, for example a GPS transponder.

The communications device may also include means for detecting when the device has been fitted to and/or removed from a medicament delivery device.

The communications device may preferably include a battery for powering the device. The battery may be a disposable battery or a rechargeable battery. Alternatively, or additionally, the communications device may obtain its operating power from the battery associated with the medicament delivery device. In such a embodiment, the medicament delivery device may be provided with a set of electrical contacts for engagement with a corresponding set of electrical contacts associated with the communications device, once the communications device has been fitted to the medicament delivery device. It is also envisaged that the battery associated with the communications device may be used to provide the operating power for the medicament delivery device and/or to recharge a battery associated with the medicament delivery device.

Examples of how the communications device may be utilised include (but are not limited to) the following examples:

In a first usage embodiment, the communications device may be used to transmit the data in real time. In such an embodiment, the communications device may be fitted to the medicament delivery device for a set length of time, and as each item of data is generated and gathered, the data may be transmitted in real time from the medicament delivery device to the communications device and subsequently wirelessly transmitted in real time to the remote location. This usage embodiment is achievable given that the communications device preferably does not in any way interfere with, or otherwise affect, the ability of the medicament delivery device to administer medicament when the communications device is fitted to the medicament delivery device (that is, the medicament delivery device may be used as normal even when the communications device is fitted thereto).

An advantage of monitoring patient usage data in real time is that patient usage data is always up to date, and hence anyone viewing or wishing to have access to the data will feel more comfort knowing this. Furthermore, any potential overuse or underuse of the medicament delivery device may be immediately apparent, and (for example) any appropriate alerts may be made to the patient (or to a third party such as a care giver or medical professional). Real time monitoring may be able to predict a potential exacerbation event, prior to the event occurring.

In a second usage embodiment, the communications device may be fitted to the medicament delivery device for a set period of time, as above, but wherein the data is transferred from the medicament delivery device to the communications device and/or from the communications device to the remote location at predetermined time intervals, for example, twice a day (in the morning and evening), or once a week, or after a certain number of doses of medicament have been dispensed. Such an arrangement may be advantageous in that the periodic transfer of data (rather than real time transfer) may extend the battery life in the medicament delivery device and/or the communications device.

In a third usage embodiment, the communications device may be attached to the medicament delivery device on an ad hoc basis, that is, whenever it is desired to transmit data from the medicament delivery device to the communications device, and thus to a remote location. For example, the patient may attach the communications device to the medicament delivery device every week, and a week's amount of patient usage data may thus be transmitted to the remote location. After the transmission of data is complete, the communications device may be removed from the medicament delivery device, and the medicament delivery device used as normal.

The first data storage means associated with the medicament delivery device may be adapted to automatically delete the data, once it has been transmitted to the communications device. Alternatively, the first data storage means may retain a copy.

The communications device may also include a second data storage means such as a memory (eg, ROM or RAM), and this memory may be adapted to likewise retain a copy of all data received and/or transmitted by the communications device. This may be useful as a backup copy of the data should the remote location not receive the data transmitted and/or if the integrity of the data is lost or affected during transmission.

Two way data transmission may be possible between the remote location and the communications device. For example, if the remote location were to receive data which was indicative of an exacerbation event, or if the patient had forgotten to take his/her medication within a predetermined time period, the remote location may be able to transmit a warning signal to the communications device (whether or not the communications device is attached to the medicament delivery device). The patient may be thus alerted to whatever event is being indicated.

PREFERRED EMBODIMENTS

The description of a preferred form of the invention to be provided herein, with reference to the accompanying drawings, is given purely by way of example and is not to be taken in any way as limiting the scope or extent of the invention.

DESCRIPTION OF PREFERRED EMBODIMENTS

Figure 2:
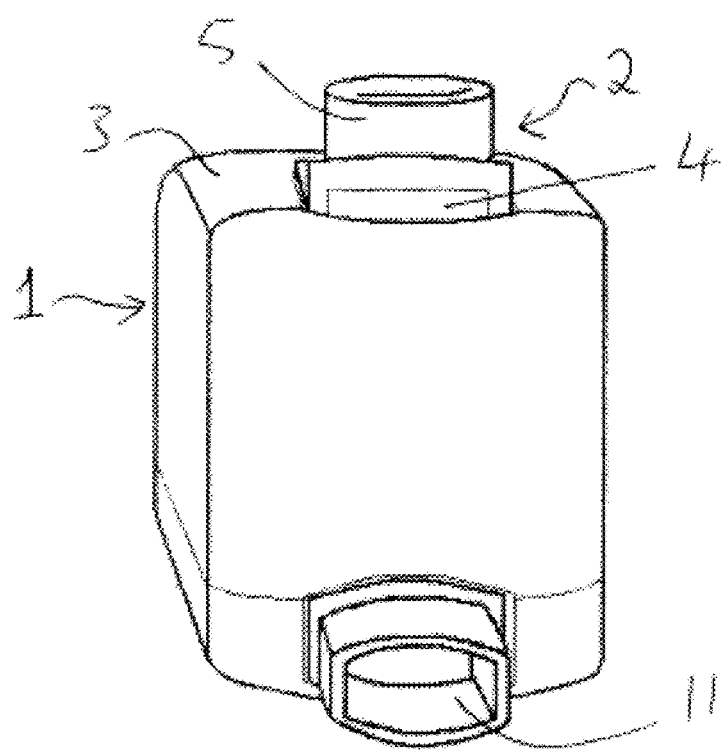
FIG. 2: is a front perspective view of the embodiment shown in FIG. 1, when attached to a pMDI electronic medicament inhaler.

Having regard to FIGS. 1 and 2, there is shown a communications device, generally indicated by arrow 1. The communications device 1 is adapted to receive and transmit data relating to patient usage of an electronic medicament inhaler 2 (see FIG. 2). The communications device 1 is adapted to be portable and reusable across a range of different medicament inhalers 2.

The device 1 includes a housing, generally indicated by arrow 3, for releasable attachment to the inhaler 2. The housing 3 is adapted to fully encircle and/or fully contain the inhaler 2.

The inhaler 2 is a pMDI inhaler which includes medicament dispensing means in the form of an actuator 4, and a supply of medicament in the form of a medicament canister 5. The inhaler 2 is for the treatment of respiratory diseases such as asthma and COPD.

The housing 3 is comprised of an injection moulded plastics material and is substantially transparent in appearance.

The housing 3 includes a main body portion 6 and a hinged body portion 7.

The main body portion 6 is substantially hollow and includes an interior portion 8 which is adapted to substantially match the exterior configuration of the inhaler 2, whereby the inhaler 2 may be snugly retained within the interior portion 8. The main body portion 6 also includes lower ledge portions 9, upon which the underside 10 of the actuator 4 rests, once the inhaler 2 has been placed within the housing 3.

In FIG. 1 the hinged portion 7 is shown in an open position which allows for the inhaler 2 to be placed within the interior portion 8 of the housing 3. Once the inhaler 2 has been placed in the interior portion 8, the hinged portion 7 is closed, as shown in FIG. 2. The hinged portion 7 is releasably secured to the main body portion 6 by the use of a latch (not shown).

It may be seen from the drawings that the housing 3 is releasably attachable to the inhaler 2, and subsequently operable, without any modifications being required to the inhaler 2. Furthermore, the inhaler 2 may be operated as normal once contained within the device 1. Moreover, the communications device 1 does not, in any way, impact upon or affect the ability of the medicament inhaler 2 to dispense medicament when fitted thereto.

Furthermore, and as may also be seen from the drawings, the fitting of the housing 3 to or around the inhaler 2 does not require the use of any tools in order to be fitted, instead the inhaler 2 is simply placed within the housing 3 of the device 1.

The inhaler 2 includes electronic data gathering means (not shown) for obtaining data in relation to patient usage of the inhaler 2. Such data gathering means for electronic inhalers are well known in the prior art and by those skilled in the art.

At the very least, the inhaler 2 will include a dose counting means and a real time clock to record the date/time of delivery of each dose of medicament.

The inhaler 2 also includes data storage means (not shown) for the storage of the patient usage data.

The inhaler 2 also includes a microprocessor (not shown) for performing operation(s) on the data.

The inhaler 2 may also include a user interface and/or audio/visual notification means and/or a battery. The communications device 1 may also include some or all of these features.

Figure 4:
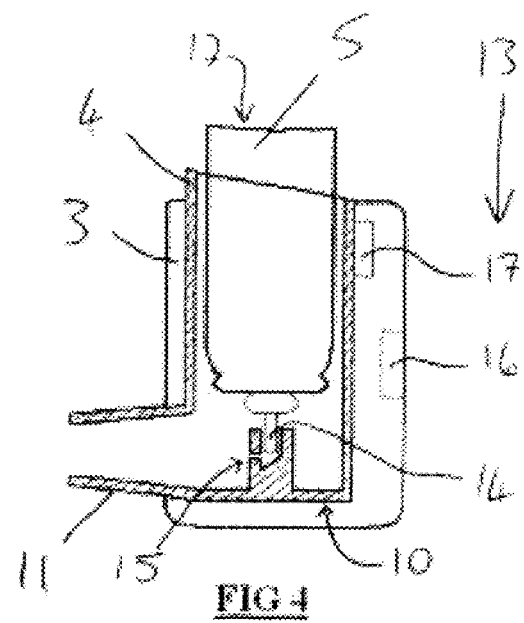

With respect to FIG. 4, when a patient wishes to dispense a dose of medicament, he/she places their mouth over the mouthpiece 11 of the actuator 4, and pushes down on the top 12 of the medicament canister 5—in the direction shown by arrow 13. This has the effect of pushing the spray stem 14 into the spray directing element 15, which releases a metered dose of medicament, which is directed out of the mouthpiece 11 and into the mouth of the patient. The patient will usually inhale strongly at the same time that the medicament is dispensed so that the medicament is inhaled deeply into the lungs of the patient.

Also with respect to FIG. 4, the communications device 1 includes an inbuilt wireless transceiver 16. The inhaler 2 includes a transceiver 17, which is integrally formed on the outside of the actuator 4. Although not shown, the inhaler transceiver 17 is in communication with either the dose counter or the data storage means so that the patient usage data may be forwarded to the inhaler transceiver 17 as or when required.

Once the communications device 1 has been fitted around the inhaler 2, the inhaler transceiver 17 may transmit the patient usage data from the inhaler 2 to the transceiver 16 of the communications device 1. This is done by using IR frequencies.

Figure 3:
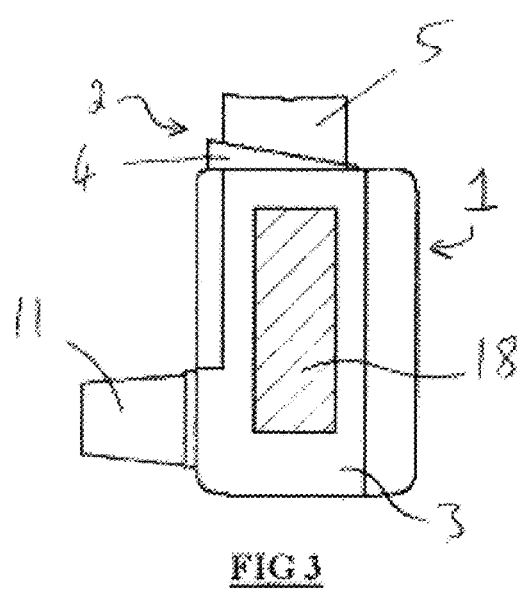
FIG. 3: is a side view of the embodiment illustrated in FIG. 2, FIG. 4: is a cut-away view of the embodiment illustrated in FIG. 3, FIG. 5: is a plan view of an alternative possible embodiment of a communications device for use with the present invention.

The communications device 1 includes an integrally formed wireless communicator in the form of a cell phone chip 18 (see FIG. 3), which is able to receive the data from the transceiver 16. The cell phone chip 18 is subsequently able to wirelessly transmit the data to a remote location such as a private or public access computer network system (eg, an intranet or the internet).

Figure 5:
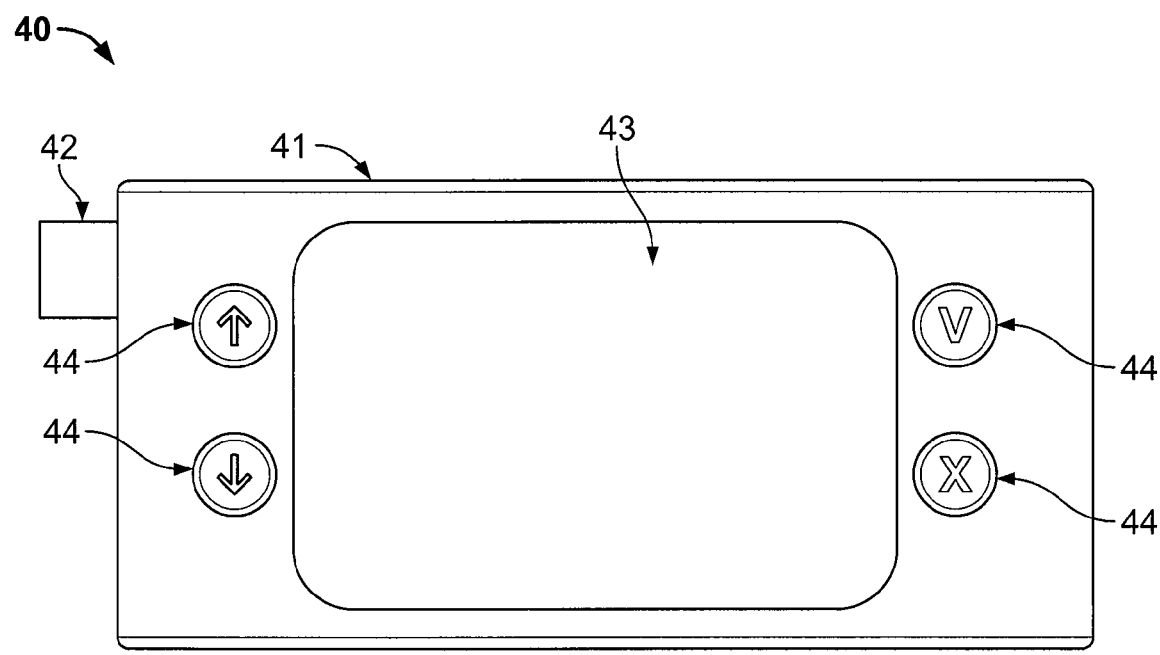

FIG. 5 illustrates another possible embodiment of the present invention. In FIG. 5 there is shown a communications device generally indicated by arrow 40. The communications device 40 operates substantially the same as the communications device 1, except that the communications device 40 is adapted to be fitted within an electronic medicament inhaler (not shown)—and in particular an electronic DPI medicament inhaler.

The communications device includes a housing 41, which has an inbuilt wireless communicator 42. The housing 41 includes a user interface in the form of a LCD screen 43 and a number of operational buttons 44. Preferably, once the communications device 40 has been fitted to an electronic medicament inhaler, the user interface may be accessible and operational. For example, the electronic medicament inhaler may be provided with a cut away portion which allows for access to the user interface, once the communications device has been fitted therein.

The communications device 40 is 54 mm in length, 36 mm in width, and 15 mm in depth.

The rear side of the communications device 40 includes a SIM card holder (not shown) for receiving a SIM card, and a PCB socket (not shown) for engaging with a complimentary PCB socket associated with the electronic medicament inhaler.

Figure 6:
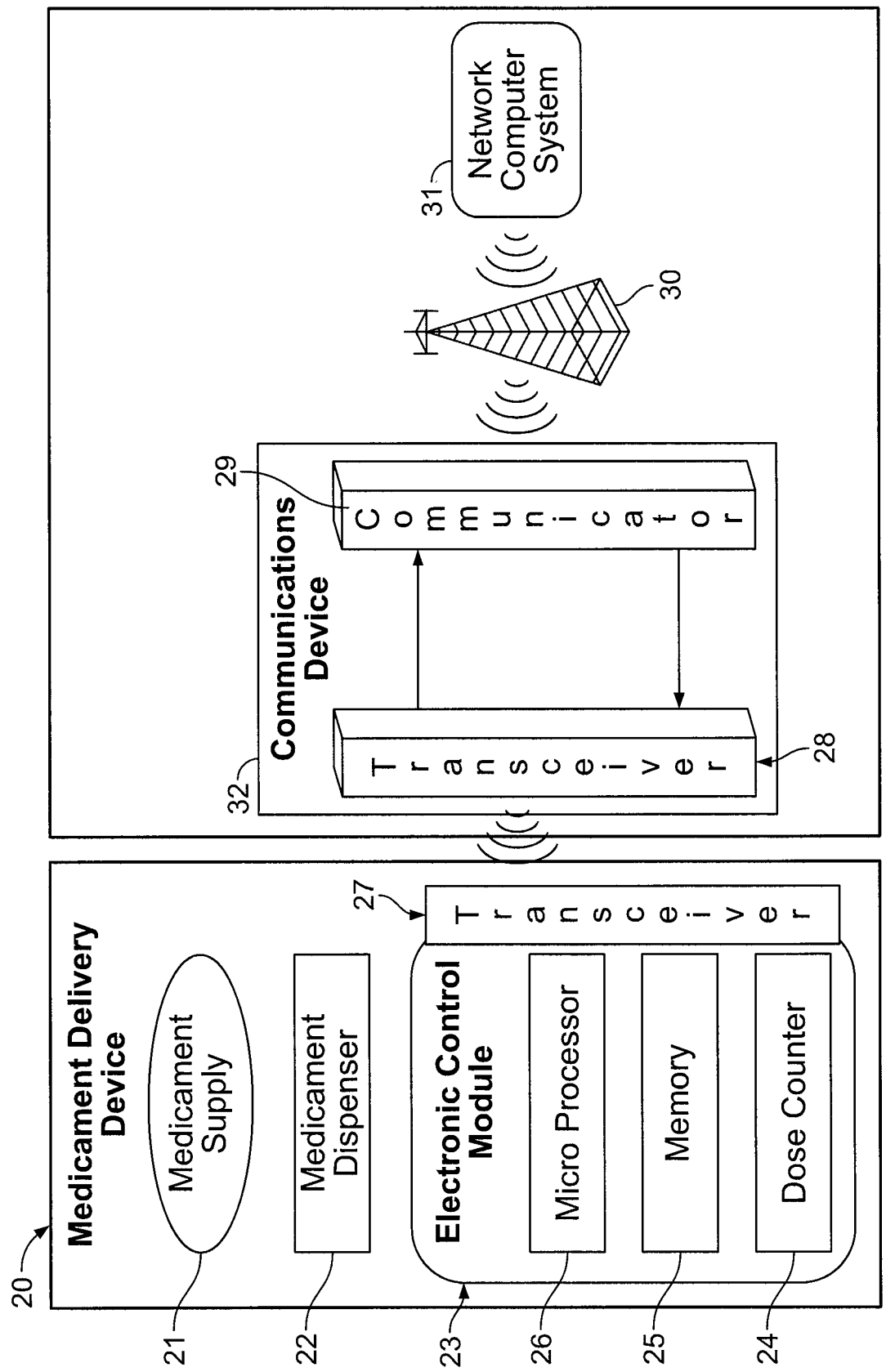
FIG. 6: is a simplified system block diagram showing the operational structure of one possible embodiment of the present invention.

FIG. 6 illustrates, in the form of a simple system block diagram, how such a communications system may work in general.

A medicament delivery device 20 is represented which includes a medicament supply 21 and a medicament dispenser 22. The medicament delivery device 20 further includes an electronic control module 23 which includes a dose counter 24, a memory 25 and a microprocessor 26.

The medicament delivery device 20 further includes a transceiver 27 for transmitting the patient usage data obtained to the transceiver 28, which is associated with the communications device 32.

The communications device 32 includes a wireless communicator 29 which is able to receive the data from the transceiver 28 and transmit it to a remote network computer system 31, via cell phone tower 30.

Two way transfer of data is possible between the network computer system 31 and the communications device 32, as well as between the communications device 32 and the medicament delivery device 20.

An advantage of the present invention is that the communications device 1 may be used to provide wireless communications ability to any electronic medicament delivery device, which would otherwise not have been able to wirelessly transmit the data captured by the medicament delivery device. Given the significant advantages of being able to wirelessly transmit patient usage data relating to a medicament delivery device (and as stated previously), this is a significant improvement over existing medicament delivery devices and related data communication systems.

Furthermore, because the communications device 32 is reusable, and across a range of different medicament delivery devices, the communications device 32 has an indefinite lifetime, which mitigates the cost of incorporating a cell phone chip within the device 32.

VARIATIONS

While the embodiments described above are currently preferred, it will be appreciated that a wide range of other variations might also be made within the general spirit and scope of the invention and/or as defined by the appended claims.

We claim:

1. A reusable and portable communications device for receiving and transmitting data relating to patient usage of an electronic medicament delivery device, said electronic medicament delivery device including:
   a) a supply of medicament,
   b) a medicament dispensing means,
   c) data gathering means for gathering data relating to patient usage of said electronic medicament delivery device,
   and wherein said communications device includes:
   d) a housing, said housing able to be releasably fitted to said electronic medicament delivery device;
   e) data collection means associated with said housing to receive said data from said electronic medicament delivery device,
   f) a wireless communicator associated with said housing to enable the wireless transmission of said data.

2. A communications device as claimed in claim 1 wherein said electronic medicament delivery device further includes a first data storage means for storing said data.

3. A communications device as claimed in claim 1, wherein said housing further includes a second data storage means for storing said data.

4. A communications device as claimed in claim 1, wherein said communications device is reusable across a range of different electronic medicament delivery devices.

5. A communications device as claimed in claim 1, wherein said housing is adapted to fully encircle and contain said electronic medicament delivery device.

6. A communications device, as claimed in claim 1, wherein said communications device is adapted to be fitted substantially within said electronic medicament delivery device.

7. A communications device, as claimed in claim 1, wherein said communications device is able to be fitted to said electronic medicament delivery device, and subsequently be operable, without any modifications being required to be made to said electronic medicament delivery device.

8. A communications device, as claimed in claim 1, wherein said communications device, once fitted to said electronic medicament delivery device, does not affect the ability of said electronic medicament delivery device to dispense medicament.

9. A communications device, as claimed in claim 1, wherein said data collection means includes a first PCB socket associated with said communications device, said first PCB socket being releasably engageable with a second PCB socket associated with said electronic medicament delivery device, wherein the mating of said first and second PCB sockets facilitates the transfer of said data from said electronic medicament delivery device to said communications device.

10. A communications device, as claimed in claim 1, wherein said data collection means includes a first wireless transceiver associated with said communications device, said first wireless transceiver being communicable with a second wireless transceiver associated with said electronic medicament delivery device, wherein said second wireless transceiver is able to transmit data from said electronic medicament delivery device to the first wireless transceiver associated with said communications device.

11. A communications device as claimed in claim 10, wherein said first wireless transceiver is able to receive said data from said second wireless transceiver from a position outside of said electronic medicament delivery device.

12. A communications device, as claimed in claim 1, wherein said data is transmitted by said communications device to a remote location.

13. A communications device as claimed in claim 12, wherein said remote location is a private or a public access computer network system.

14. A communications device as claimed in claim 12, wherein said remote location is at least one web service.

15. A communications device, as claimed in claim 1, wherein said electronic medicament delivery device further includes an electronic control module for controlling the operation of said electronic medicament delivery device.

16. A communications device as claimed in claim 1, wherein said communications device further includes an electronic control module for controlling the operation of said communications device and/or said electronic medicament delivery device.

17. A communications device, as claimed in claim 1, wherein said communications device is further adapted to be able to transmit data or instructions to said electronic medicament delivery device.

18. A communications device as claimed in claim 1, wherein said electronic medicament delivery device includes a battery, said battery being adapted to provide power to said communications device once said communications device has been fitted to said electronic medicament delivery device.

19. A communications device as claimed in claim 1, wherein said electronic medicament delivery device is an electronic medicament inhaler.

* * * * *